US00PP32125P2

(12) United States Plant Patent
Snijder

(10) Patent No.: US PP32,125 P2
(45) Date of Patent: Aug. 25, 2020

(54) ***PELARGONIUM* PLANT NAMED 'PEQZ0062'**

(50) Latin Name: *Pelargonium interspecific*
Varietal Denomination: PEQZ0062

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,594

(22) Filed: May 6, 2019

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0062' particularly distinguished by the has pink colored inflorescences with semi double florets held above dark green foliage on well-branched semi-trailing to trailing plant habit.

1 Drawing Sheet

Latin name of the genus and species of the plant claimed: *Pelargonium interspecific.*

Varietal denomination: 'PEQZ0062'.

BACKGROUND OF THE NEW PLANT

The present invention comprises a new *Pelargonium*, botanically known as *Pelargonium interspecific*, and hereinafter referred to by the variety name 'PEQZ0062'.

'PEQZ0062' is a product of a planned breeding program. The new cultivar 'PEQZ0062' has pink colored inflorescences with semi double florets held above dark green foliage on well-branched semi-trailing to trailing plant habit.

'PEQZ0062' originates from a hybridization in a controlled breeding program made in February 2014, in a greenhouse in Amatitlán, Guatemala. The female parent was a patented plant of *P. peltatum* parentage (described in U.S. Pat. No. 27,537), identified as 'PEPZ0005' with single flowered florets and lighter green colored foliage when compared to 'PEQZ0062'.

The male parent of 'PEQZ0062' was an unpatented, proprietary plant of *P. interspecific* parentage, identified as 'PEL-AY2177-09' with more blue-rose colored florets when compared to 'PEQZ0062'. The resultant seed was sown in December 2014.

'PEQZ0062' was selected as one flowering plant within the progeny of the stated cross in April 2015 in a greenhouse in Enkhuizen, The Netherlands.

The first act of asexual reproduction of 'PEQZ0062' was accomplished when vegetative cuttings were propagated from the initial selection in June 2015 in a greenhouse in Enkhuizen, The Netherlands.

BRIEF SUMMARY OF INVENTION

Horticultural examination of plants grown from cuttings of the plant initiated in June 2015 in Enkhuizen, the Netherlands, and continuing thereafter, has demonstrated that the combination of characteristics as herein disclosed for 'PEQZ0062' are firmly fixed and are retained through successive generations of asexual reproduction.

'PEQZ0062' has not been observed under all possible environmental conditions. The phenotype may vary significantly with variations in environment such as temperature, light intensity, and day length.

A Plant Breeder's Right for this cultivar has not yet been applied for. 'PEQZ0062' has not been made publicly available prior to the effective filing date of this application, notwithstanding any disclosure that may have been made less than one year prior to the effective filing date of this application by the inventor or another who obtained 'PEQZ0062' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0062' with colors being as true as possible with an illustration of this type.

Figure 1:
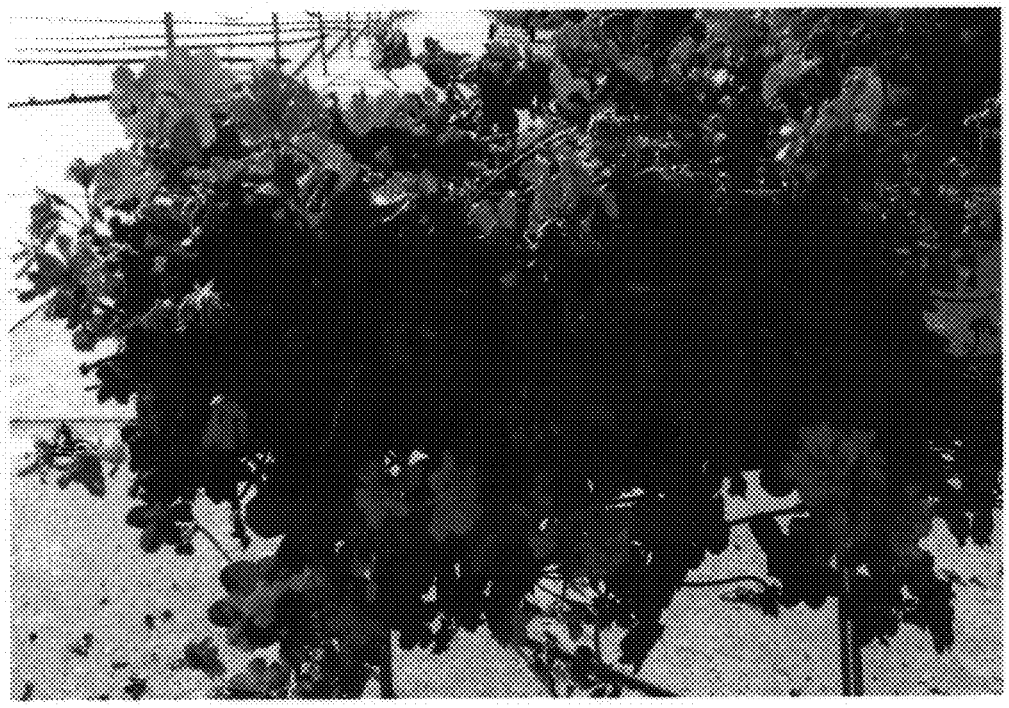
Figure 2:
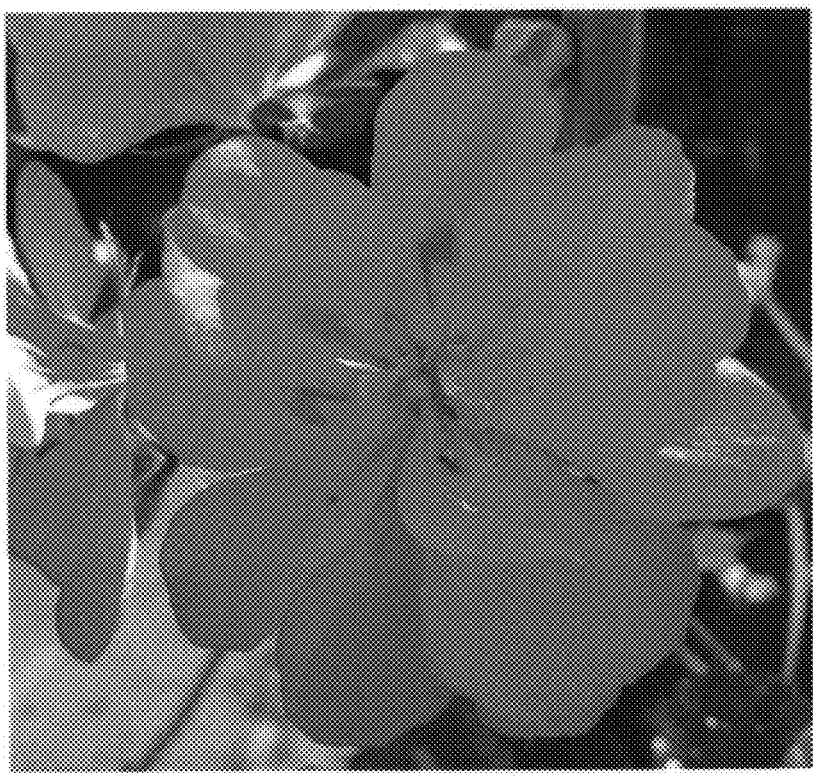

The photographic drawings in FIG. 1 shows a basket with 4 flowering plants of the new variety and in FIG. 2, a close-up of the flower.

DETAILED BOTANICAL DESCRIPTION

The plant descriptions and measurements were taken in Andijk, the Netherlands Oktober under natural light. These plants were approximately 14 weeks old and were grown in a 1 gallon pots, in a greenhouse trial. The plants shown in the photographs were about 25 weeks old growing in a 10 inch pot in a greenhouse. The photographs were taken in October 2018.

Color references are made to The Royal Horticultural Society Colour Chart (R.H.S.) 2001.

TABLE 1

DIFFERENCES BETWEEN THE NEW VARIETY 'PEQZ0062' AND TWO MOST SIMILAR VARIETIES

| | 'PEQZ0062' | 'Fisrimba' (U.S. Plant Pat. No. 12,355) | 'Fislamda' (U.S. Plant Pat. 12,225) |
|---|---|---|---|
| Foliage color: | Dark green up to RHS 147A | Medium green RHS 137D | Color of upper surface: Medium green, RHS 137 B-C. Color of lower surface: RHS 137D. |
| Flower color when observed from a distance | Red tinge | Rose tinge | Purple tinge |
| Plant vigor | Medium vigor | Medium vigor | Low vigor |
| Foliage color observed from a distance when exposed to high summer heat | Stable green color or only fading slightly | Fading to yellow green | Fading to yellow |

Plant:

*Form, growth and habit.*—Semi-upright, semi-trailing.

*Plant height.*—14-18 cm.

*Plant height (inflorescence included).*—18-22 cm.

*Plant width.*—35-40 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—Between RHS 137C and RHS 143A.

*Immature leaf, lower surface.*—Between RHS 137C and RHS 143A, however slightly lighter than upper surface.

*Mature leaf, color upper surface.*—Closest to RHS 137A and RHS 147A.

*Mature leaf, color lower surface.*—Closest to RHS 137B and RHS 137C.

*Length.*—About 5.0-5.5 cm.

*Width.*—About 8.0-9.0 cm.

*Shape.*—Orbicular, with wavy lobs.

*Base shape.*—Cordate, heart-shaped.

*Apex shape.*—Rounded, waved.

*Margin.*—Wavy, undulate margins.

*Texture upper side.*—Pilose.

*Texture lower side.*—Pilose.

*Leaf zonation color.*—RHS 202A.

*Variegation of the leaf blade.*—Absent.

*Color of veins, upper surface.*—Closest to RHS 144B and RHS 144C, becoming indistinct.

*Color of veins, lower surface.*—Closest to RHS 144B and RHS 144C, becoming indistinct.

*Pattern of veining.*—Palmate.

*Petiole color.*—Closest to RHS 144A and RHS 144B.

*Petiole length.*—Range: 2.0-7.0 cm.

*Diameter of petiole.*—0.2-0.3 cm.

*Texture.*—Pilose, hirsute hairs.

Stem:

*Quantity of branches.*—7-9.

*Color of stem/branches.*—Closest to RHS 187A and RHS 187B parts of stem/branches with strong anthocyanins), closest to RHS 144A and RHS 144B (green parts).

*Length of stem/branches.*—30-40 cm.

*Diameter.*—0.5-0.6 cm.

*Length of internodes.*—2-6 cm.

*Texture.*—Pilose, hirsute hairs.

Peduncle:

*Color of peduncle.*—Closest to RHS 144A and RHS 144B with strong anthocyanins closest to RHS 187A and RHS 187B.

*Length of peduncle.*—Range: 9-16 cm.

*Peduncle diameter.*—0.3-0.4 cm.

*Texture.*—Hirsute.

Pedicel:

*Color of pedicel.*—Closest to RHS 187A and RHS 187B.

*Length of pedicel.*—2.0-2.2 cm.

*Diameter of pedicel.*—0.15-0.2 cm.

*Texture.*—Pilose.

Bud (just before opening):

*Color.*—Margins petals just before opening closest to RHS 57A, but much whiter in the middle.

*Length.*—About 1.5 cm.

*Width.*—0.7-0.8 cm.

*Shape.*—Elliptical.

Inflorescence:

*Type.*—Umbel, semi-spherical.

*Lastingness of individual flowers.*—7-9 days at 18° C. temperature.

*Number of inflorescences per plant.*—6 mature and 20 immature umbels in various stages.

*Fragrance.*—None.

*Umbel diameter.*—8.0-10.0 cm.

*Umbel depth.*—5.0-6.0 cm.

Corolla:

*Form.*—Semi-double.

*Number of petals.*—12.

*Diameter of flower.*—4.5-5.5 cm.

*Depth of flower.*—2-2.5 cm.

*Color upper petals, upper surface.*—Closest to RHS 66A, but with a slightly more violet tone.

*Color upper petals, lower surface.*—Closest to RHS 66D but whiter.

*Length of upper petals.*—3.0 cm.

*Width of upper petals.*—1.5 cm.

*Color lower petals, upper surface.*—Closest to RHS 66A, but with a slightly more violet tone.

*Color lower petals, lower surface.*—Closest to RHS 66D but whiter.

*Length of lower petals.*—2.7 cm.

*Width of lower petals.*—1.5 cm.

*Petal shape.*—Obovate to spatulate.

*Apex shape.*—Rounded.

*Margin.*—Entire.

*Base.*—Attenuate.

*Petal texture.*—Papillose.

Calyx:

*Number of sepals.*—5.

*Color of sepals.*—Closest to RHS 144A and RHS 144B, covered with anthocyanins closest to RHS 187A.

*Length of sepals.*—1.7 cm.

*Width of sepals.*—0.3-0.4 cm.

*Sepal shape*.—Lanceolate to enciform.
*Apex shape*.—Acute, with a sharp tip.
*Margins*.—Entire.
*Texture, upper surface*.—Pilose.
*Lower surface*.—Pilose.

Reproductive organs:

Gynoecium:

*Pistil*.—1.
*Length*.—1-1.1 cm.
*Style color*.—Closest to RHS 145D.
*Style length*.—0.5-0-6 cm.
*Stigma color*.—Closest to RHS 60A.
*Ovary color*.—Closest to 145A.
*Ovary length*.—0.4-0.5 cm.
*Ovary diameter*.—About 0.3 cm.

Androecium:

*Number of stamens*.—5.
*Color of filaments*.—Closest to RHS 66A, at base: closest to RHS 155C.
*Length filaments*.—1.0-1.2 cm.
*Anther color*.—Closest to RHS 70A, margins closest to RHS 81A.
*Length of anthers*.—About 0.3 cm.
*Color of pollen*.—Closest to RHS 28A.
*Pollen amount*.—Moderate.
*Fertility/seed set*.—Has not been determined to date.
*Disease/pest resistance*.—Has not been determined to date.

What is claimed is:

1. A new and distinct variety of *Pelargonium* plant named 'PEQZ0062' substantially as illustrated and described herein.

* * * * *